United States Patent
Borovsky

Patent Number: 6,080,361
Date of Patent: *Jun. 27, 2000

[54] CONTACT LENS CLEANING AND DISINFECTING SYSTEM

[76] Inventor: Simcha Borovsky, 17-25 Hunter Pl., Fair Lawn, N.J. 07410

[*] Notice: This patent issued on a continued prosecution application filed under 37 CFR 1.53(d), and is subject to the twenty year patent term provisions of 35 U.S.C. 154(a)(2).

[21] Appl. No.: 08/935,047

[22] Filed: Sep. 22, 1997

[51] Int. Cl.$^7$ ................ A61L 12/02; B08B 3/14
[52] U.S. Cl. ............... 422/1; 422/300; 134/10; 134/34; 134/111; 134/901
[58] Field of Search .................... 422/28, 31, 116, 422/292, 300, 1; 134/111, 901, 10, 34, 42

[56] References Cited

U.S. PATENT DOCUMENTS

| | | | |
|---|---|---|---|
| 4,601,300 | 7/1986 | Sundheimer | 134/111 X |
| 4,615,799 | 10/1986 | Mortensen | 422/24 X |
| 4,714,558 | 12/1987 | Barbee et al. | 134/111 X |
| 5,039,349 | 8/1991 | Schoeppel | 134/111 X |
| 5,082,558 | 1/1992 | Burris | 422/300 X |
| 5,144,144 | 9/1992 | Borovsky | 422/24 X |
| 5,431,897 | 7/1995 | Heyl et al. | 422/300 |
| 5,515,877 | 5/1996 | Dunn, Jr. | 134/111 |
| 5,630,436 | 5/1997 | Chase | 134/111 |
| 5,709,235 | 1/1998 | Akanuma et al. | 134/111 |

*Primary Examiner*—Elizabeth McKane
*Attorney, Agent, or Firm*—Baker Botts L.L.P.

[57] ABSTRACT

A system and method for cleaning, disinfecting and storing contact lens in an all-in-one unit is provided. The system employs preservative-free saline solution, a disposable bacteriological filter and a pump to provide a portable and lightweight system. The cleaning and disinfecting steps are completed in a few minutes, after which the system automatically shuts off. The cleaned and disinfected lenses can be stored in the unit overnight without the need for the user to handle the lenses after the system shuts off.

18 Claims, 3 Drawing Sheets

CONTACT LENS CLEANING AND DISINFECTING SYSTEM

BACKGROUND OF THE INVENTION

This invention relates to a contact lens cleaning and disinfecting system and, more particularly, a contact lens cleaning and disinfecting system which provides cleaning, disinfection and storage in an all-in-one unit.

Contact lenses have become widely used, and advanced lens materials and care products have been introduced years ago. However, proper care still remains an expensive and time consuming process which tends to discourage potential users or causes users not to follow recommended care procedures. Proper contact lens care should include the steps of (1) removing foreign particles, smoke film, and other deposits such as mucous, proteins, and enzymes from the lenses and (2) disinfecting organisms in the deposits and on the lenses to prevent eye infections from their subsequent use. Disinfection is particularly important for the use of "soft" contact lens (hydrophilic) which are able to absorb moisture from cleaning solutions.

The conventional cleaning process includes a daily regime of the lens scrubbing (by manual rubbing) with a soap or detergent, followed by rinsing with water. The use of tap water is not recommended due to the presence of hard minerals in most tap water. Besides being inconvenient, the manual rubbing and handling of the lens during cleaning can cause scratches or microscopic damage to the lens. The lens must then be disinfected, by soaking it in a chemical solution and/or by heating for as long as six hours or overnight. The disinfection step is long, and the chemical solution usually contains detergents, enzyme removers, preservatives, and other chemicals which can be absorbed into the lens and become very irritating to the eyes and membranes. Heat disinfection is generally not effective for cleaning deposits from the lens, but rather tend to bake mineral deposits onto the lens surface. Also, repeated heating of the lens for the disinfection step eventually causes physical degradation of the lens material.

Examples of prior attempts to provide an improved system for cleaning and/or disinfecting contact lens are described in many U.S. patents. These patents have focused primarily on improvements to the chemical system used for disinfecting the lens or on the manner in which the contact lens is exposed to the chemical system.

For example, the system disclosed in U.S. Pat. No. 5,320,806 (Dziabo et al.) employs a liquid electrolyte containing a chlorine dioxide precursor. By passing electric current through the liquid electrolyte a disinfectant of chlorine dioxide is formed. Chlorine dioxide is described in the patent as being less irritating to the eyes than conventional chemical solutions.

The system disclosed in U.S. Pat. No. 5,082,558 (Burris) employs an ozone generator and a pumping system that mixes the generated ozone with a purifying liquid and brings them into contact with the contact lens.

The system disclosed in U.S. Pat. No. 4,852,592 (DiGangi et al.) employs a plurality of disposable solution containers for sequential cleaning cycles using daily cleaning solution, enzymatic solution, disinfecting solution and saline/neutralizing solution. A timing cycle module provides sequential fluid supply both to and from a cleaning chamber (where the contact lens are positioned) and controls agitation of the lens.

The system disclosed in U.S. Pat. No. 4,36,536 (Leopardi) employs carbon dioxide at high pressure for a period of at least twenty (20) minutes to affect sterilization.

The above systems are still too complex, generally expensive to manufacture and have not achieved commercial success. Moreover, they all employ solutions that can be irritating to the eyes and membranes since they inherently involve the use of disinfecting chemical processes. Accordingly, there is still a need for an improved system for cleaning and disinfecting contact lens, particularly one that is an all-in-one unit.

In light of the above, it would be desirable to be able to provide a contact lens cleaning and disinfecting system which does not utilize irritating chemicals, preservatives, detergents, or enzyme removers.

It would also be desirable to be able to provide a contact lens cleaning and disinfecting system which cleans deposits in a hands-free process from the contact lens in a relatively short time.

It would further be desirable to be able to provide a contact lens cleaning and disinfecting system which can disinfect the lens without the need for a time-consuming heating step or the use of disinfectant chemical solutions.

It would still further be desirable to be able to provide a contact lens cleaning and disinfecting system that is inexpensive to manufacture and easy and convenient for a user to operate.

SUMMARY OF THE INVENTION

It is an object of this invention to provide a contact lens cleaning and disinfecting system which does not utilize irritating chemicals, preservatives, detergents, or enzyme removers.

It is also an object of this invention to provide a contact lens cleaning and disinfecting system which cleans deposits in a hands-free process from the contact lens in a relatively short time.

It is a further object of this invention to provide a contact lens cleaning and disinfecting system which can disinfect the lens without the need for a time-consuming heating step or the use of disinfectant chemical solutions.

It is a still further object of this invention to provide a contact lens cleaning and disinfecting system that is inexpensive to manufacture and easy and convenient for a user to operate.

In accordance with the present invention there is provided a contact lens cleaning and disinfecting system. The system includes a cleaning chamber for holding the contact lens in a volume of solution; a recovery chamber for recovering solution removed from the cleaning chamber; a pumping chamber including a pump for (1) injecting solution into the cleaning chamber for cleaning said contact lens and (2) causing solution to flow from the cleaning chamber to the recovery chamber; and a bacteriological filter coupled between the recovery chamber and the pumping chamber for removing microorganisms from the solution, whereby the pump is used to recirculate the solution in the system while trapping microorganisms onto the filter.

The present invention also includes a method for cleaning and disinfecting a contact lens. The method includes the steps of: (a) placing the lens in a cleaning chamber of a unit; (b) filling the chamber with a solution; (c) activating an impeller for injecting solution into the cleaning chamber for cleaning said contact lens; (d) trapping microorganisms on a bacteriological filter; and (e) recirculating the solution through the unit. In accordance with the present invention, the filter is replaced periodically to remove the microorganisms from the unit.

BRIEF DESCRIPTION OF THE DRAWINGS

The above and other objects and advantages of the invention will be apparent upon consideration of the following detailed description, taken in conjunction with the accompanying drawings, in which like-reference numerals refer to like-parts throughout, and in which.

DETAILED DESCRIPTION OF THE INVENTION

Figure 1:
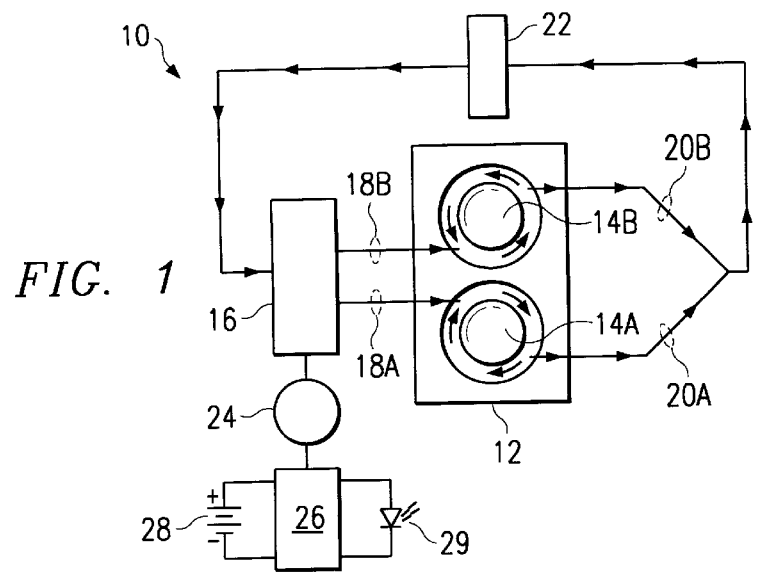
FIG. 1 is a schematic block diagram of the contact lens cleaning and disinfecting system of the present invention.

FIG. 1 is a schematic block diagram of the contact lens cleaning and disinfecting system of the present invention. System 10 includes a cleaning chamber 12 for holding contact lenses 14A and 14B. Recirculation pump 16 is used to inject solution into cleaning chamber 12 through injection channels 18A and 18B associated with lenses 14A and 14B, respectively. Coupled to cleaning chamber 12 are a pair of collecting channels 20A and 20B for collecting used (contaminated) solution from chamber 12. In turn, collecting channels 20A and 20B are coupled to bacteriological filter 22. As the solution is passed through filter 22 it is recirculated through the system by way of pump 16. Motor 24 is used to drive pump 16. System 10 is controlled by control circuit 26 which is powered by battery 28. LED 29 is used an as indicator to inform the user whether or not the system is activated.

System 10 works as follows. A user places a pair of contact lenses in cleaning chamber 12 which is filled with an ophthalmic solution (preferably a preservative-free saline solution). Upon activation, pump 16 injects fresh disinfected solution into cleaning chamber 12 (by way of injecting channels 18A and 18B) with a relatively high-pressure jet stream. This creates a vigorous swirling effect in chamber 12 around the lenses at a solution velocity sufficient to remove and rinse away protein deposits, particles, films or other deposits harboring on the lenses. Microorganisms bonded to protein deposits or on the lens surface is rinsed away from the lenses into the solution current through collecting channels 20A and 20B.

Collecting channels 20A and 20B collect and direct the solution from cleaning chamber 12 through bacteriological filter 22 (preferably of the type used in microbiological analysis products having a mesh size of about 0.5 microns). Filter 22 traps microorganisms that were dislodged from the contact lenses and carried into the solution current. This permits a substantially bacteria-free solution to flow to the low-pressure side of filter 22 back into pump 16 where the above process is repeated until control circuit 26 deactivates motor 24, which runs pump 16.

Because the removal of the lens contaminants is relatively quick and microorganisms are trapped on filter 22, there is generally no need for any additional disinfecting steps used to kill microorganisms. In the prior art, a heating or irradiation step, or a chemical-solution soaking step, is typically used to kill microorganisms. In contrast, in accordance with the present invention, preservative-free saline solution can be used, eliminating the need to use harsh chemicals that generally irritate the eyes. Also, because of the swirling action effect in the cleaning chamber, the system does not require that the lens be "manually rubbed" prior to use as in the prior art. In addition, because of the system's unique arrangement, the cleaning and disinfecting process can be completed in only a few minutes (e.g., 3 to 5).

Thus, an improved system for cleaning and disinfecting contact lens has been provided.

Figure 2:
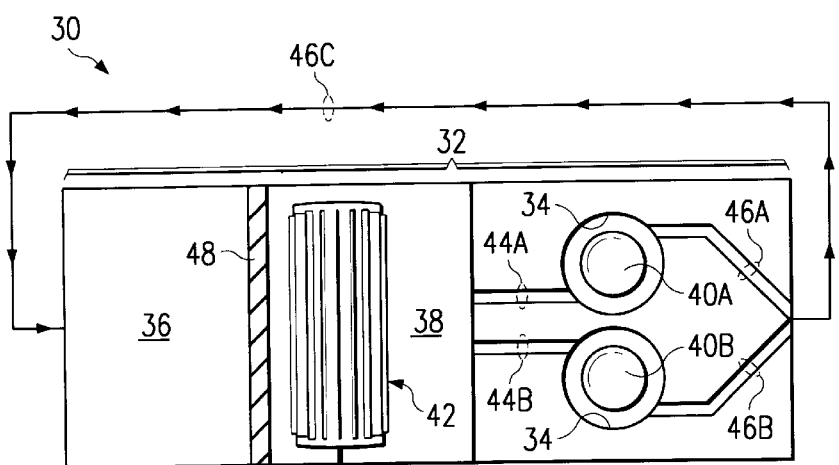
FIG. 2 is a block diagram of a preferred embodiment of the contact lens and disinfecting system of the present invention.

FIG. 2 is a block diagram of a preferred embodiment 30 of the contact lens and disinfecting system of the present invention. In accordance with this embodiment of the invention, system 30 includes solution chamber 32 which comprises three separate chambers: cleaning chamber 34, recovery chamber 36 and pump chamber 38. Cleaning chamber 34 is used to hold contact lenses 40A and 40B for cleaning and disinfecting. Pump chamber 38 is used to pump solution into cleaning chamber 34 through the use of impeller 42 which is rotated at high speed by motor 44. The solution is injected into cleaning chamber 34 by way of injection channels 44A and 44B associated with lenses 40A and 40B. Collecting channels 46A and 46B, in conjunction with collection line 46C, are used for collecting used solution from cleaning chamber 34 and recirculating the solution to recovery chamber 36. Coupled between recovery chamber 36 and pump chamber 38 is bacteriological filter 48.

In accordance with the present embodiment of the invention, because of the particular arrangement of impeller 42 and filter 48 within solution chamber 32, system 30 provides for an efficient means of cleaning and disinfecting contact lenses in a relatively short time without the need to use a chemical disinfectant or an overnight soaking step as in the prior art. This results in a design that is not only convenient and safe to use, but relatively inexpensive to manufacture as well.

In particular, because of the arrangement of a high-speed impeller adjacent injecting channels 44A and 44B, a high velocity swirling effect is created and localized in cleaning chamber 34 where protein deposits, particles, films or other deposits are removed from the lens. This process eliminates the need for a user to manually scrub the lenses prior to further disinfecting and cleaning which was typically required by the prior art.

Moreover, because of the use of a bacteriological filter 48 that is spaced-away from cleaning chamber 34, microorganisms can be effectively isolated from recirculation in the system so as to provide a system that continually exposes the contact lenses to a clean or fresh supply of solution without the need to use large volumes of solution (which can be wasteful, not to mention expensive to the user). Filter 48 effectively isolates (in recovery chamber 36) the microorganisms removed from the lens where they are prevented from diffusing or migrating into pump chamber 38 because of their inability to flow through the small mesh size (e.g., 0.5 micron) of filter 48. This process eliminates the need to use a chemical disinfectant, heating or irradiation step to remove microorganisms from the contact lenses which was typically required by the prior art. Moreover, it is much quicker to use since the whole process can be completed in only a few minutes (in contrast to the hours previously required by other methods).

Figure 3:
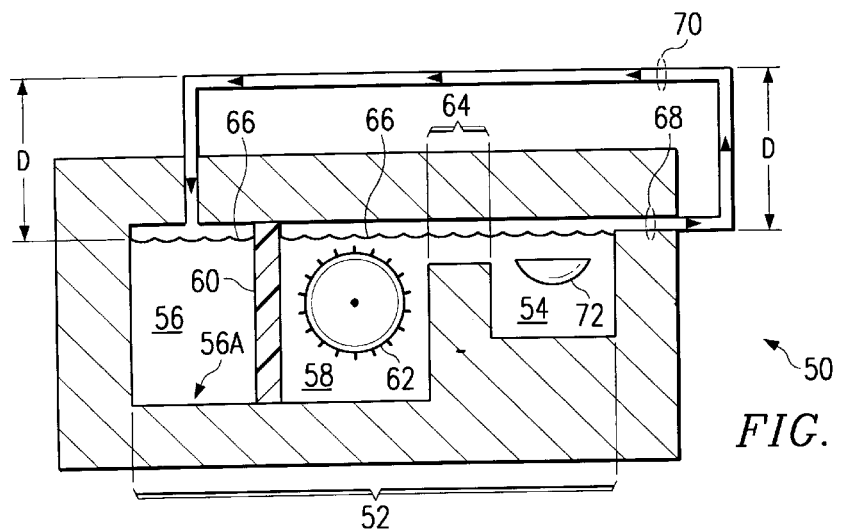
FIG. 3 is a diagram illustrating a preferred embodiment of the present invention for effectively isolating microorganisms (removed from the surface of contact lenses to be cleaned) in a recovery chamber to trap the removed deposits and recover the solution.

As discussed above, the bacteriological filter is spaced-away from the cleaning chamber in order to effectively isolate microorganisms in the recovery chamber. In accordance with another aspect of the present invention, FIG. 3 is a diagram illustrating a preferred embodiment for achieving such isolation. System 50 (as is the case with system 30 shown in FIG. 2) includes a solution chamber 52 comprised of three separate chambers: cleaning chamber 54, recovery chamber 56 and pump chamber 58. Filter 60 separates recovery chamber 56 from pump chamber 58 (which includes impeller 62. The solution is injected into cleaning chamber 54 by way of injection channel 64 (which has a smaller cross-sectional area than pump chamber 58 to provide the high-velocity swirling effect in cleaning chamber 54).

As shown in FIG. 3, cleaning chamber 54, recovery chamber 56 and pump chamber 58 are all in fluid communication with each other after solution chamber 52 is filled with solution. (This is shown in the figure by way of surface line 66, which is intended to illustrate the surface of the solution after the three chambers are initially filled.) In accordance with the present invention, collection channel 68 and solution recovery line 70 are used to provide recirculation of solution from cleaning chamber 54 to recovery chamber 56. As shown in FIG. 3, solution recovery line 70 is arranged at a height D above surface line 66 so that when system 50 is not activated, gravity prevents the solution in recovery chamber 56 from back-flowing into cleaning chamber 54 by way of recovery line 70 and collecting channel 68. This feature of the present invention provides for an effective means of isolating microorganisms to recovery chamber 56 and on the low-pressure side (i.e., non-pump side) of filter 60. Moreover, because of the arrangement shown in FIG. 3, recovery chamber 56 allows heavy contaminants to settle on its bottom surface 56A so as to prevent them from being recirculated in the system.

During activation of system 50, impeller 62 rotates at a speed sufficient to clean contact lens 72 and allow the solution in cleaning chamber 54 to flow through collecting channel 68 and recovery line 70 back to recovery chamber 56. After impeller 62 is deactivated, any solution present in recovery line 70 will flow (due to gravity) back into solution chamber 52. This will cause recovery line 70 to "dry out" and effectively prevent any microorganisms present in recovery chamber 56 (or on filter 60) to back-flow or migrate into cleaning chamber 54 where the cleaned contact lens can be stored in a disinfected environment until the user desires to remove the lens from cleaning chamber 54 (e.g., the next day).

Thus, as illustrated in FIG. 3, a system and method for isolating microorganisms (removed from the surface of contact lenses) to a spaced-away and remote part of a solution chamber has been disclosed. This system and method allows a user to clean and disinfect contact lenses by simply (1) placing the lenses in the system; (2) filling a three-part chamber with solution; and (3) activating an impeller for a few minutes. Because of the design of the system, a single, preservative-free, saline solution can be used for both cleaning and disinfecting the lenses without the need for (i) a manual finger-rubbing step or (ii) an overnight soaking step. In addition, if desired, after the lenses are cleaned and disinfected, the user can allow the lenses to remain in the system overnight without being required to remove them from the system or store them in another disinfected environment.

Figure 4A:
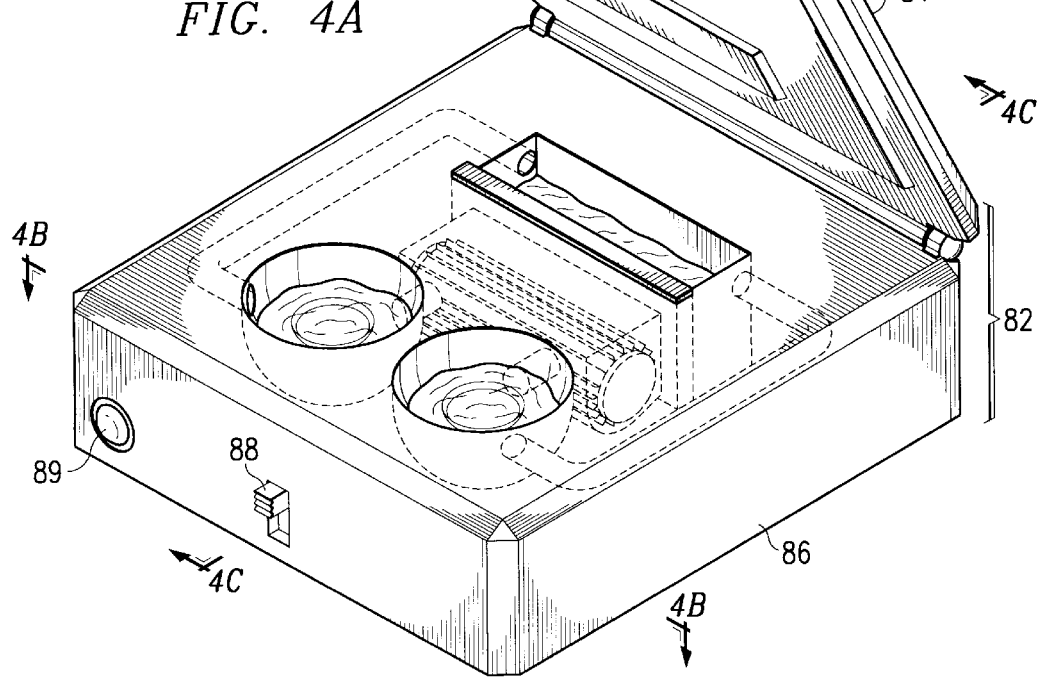
FIG. 4A is a perspective view of another preferred embodiment of the contact lens cleaning and disinfecting system of the present invention.
Figure 4B:
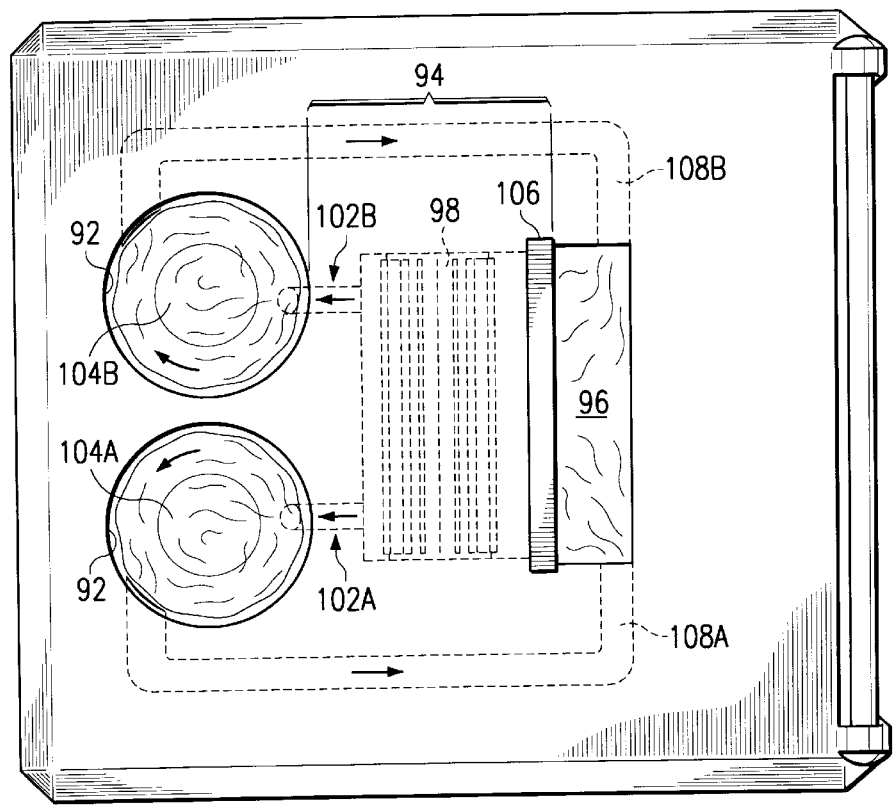
FIG. 4B is a top view of the base portion of the contact lens cleaning and disinfecting system of FIG. 4A taken from line 4B—4B of FIG. 4A.
Figure 4C:
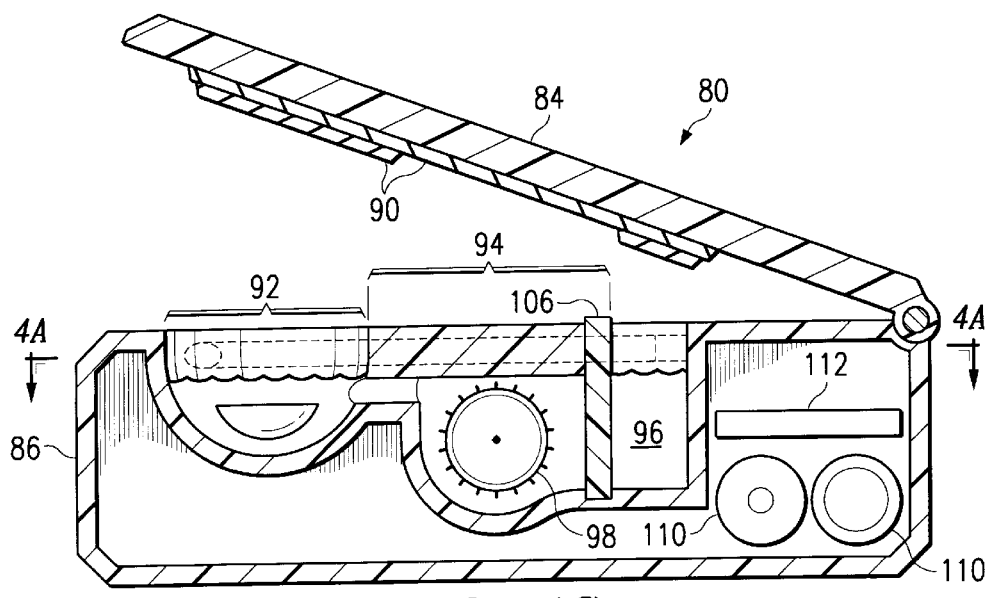
FIG. 4C is a side sectional view of the contact lens cleaning and disinfecting system of FIG. 4A taken from line 4C—4C of FIG. 4A.

In accordance with another aspect of the present invention, there is also provided a contact lens cleaning and disinfecting system that is compact, portable and lightweight. FIGS. 4A, 4B and 4C illustrate this embodiment of the present invention. System 80 includes a housing 82 having lid 84 and base unit 86. Lid 84 is hinged to allow the lid to be opened and closed. On the front face of base unit 86 is an ON/OFF switch 88 for activating the system and LED indicator 89 for indicating its status.

As illustrated in FIGS. 4B and 4C, system 80 includes three chambers: cleaning chamber 92, recovery chamber 94 and pump chamber 96 (as discussed above in connection with FIGS. 2 and 3). Pump chamber 96 includes impeller 98 used to inject solution into cleaning chamber 92 by way of injecting channels 102A and 102B (associated with contact lenses 104A and 104B, respectively). Bacteriological filter 106 is coupled between recovery chamber 94 and pump chamber 96. Collecting channels 108A and 108B (associated with contact lenses 104A and 104B, respectively) are used for collecting used solution from cleaning chamber 92 and recirculating the solution to recovery chamber 96. In accordance with the above discussion of FIG. 3, collecting channels 108A and 108B are arranged at a height above the solution level in system 80 to provide effective isolation of cleaning chamber 92 from recovery chamber 96 when the system is deactivated (e.g., overnight when the lenses are being stored for subsequent use).

Attached to the underside of lid 84 is a form-fitting gasket 90 which is used to prevent the leakage of solution (1) between recovery chamber 96 and pump chamber 94 without passing through filter 106, (2) between pump chamber 94 and cleaning chamber 92 without passing through injecting channels 102A and 102B or (3) outside the housing when the lid is closed. Gasket 90 is also used to ensure that the overall level of the solution in the three chambers 92, 94 and 96 is lower than the height of collection channels in accordance with FIG. 3. System 80 is powered by a pair of batteries 110 and controlled by control circuit 112. If desired, an adapter can be used to power system 80 from an AC source.

Thus, a compact, portable and lightweight system for cleaning, disinfecting and storing a pair of contact lenses in an all-in-one unit has been provided.

Figure 5:
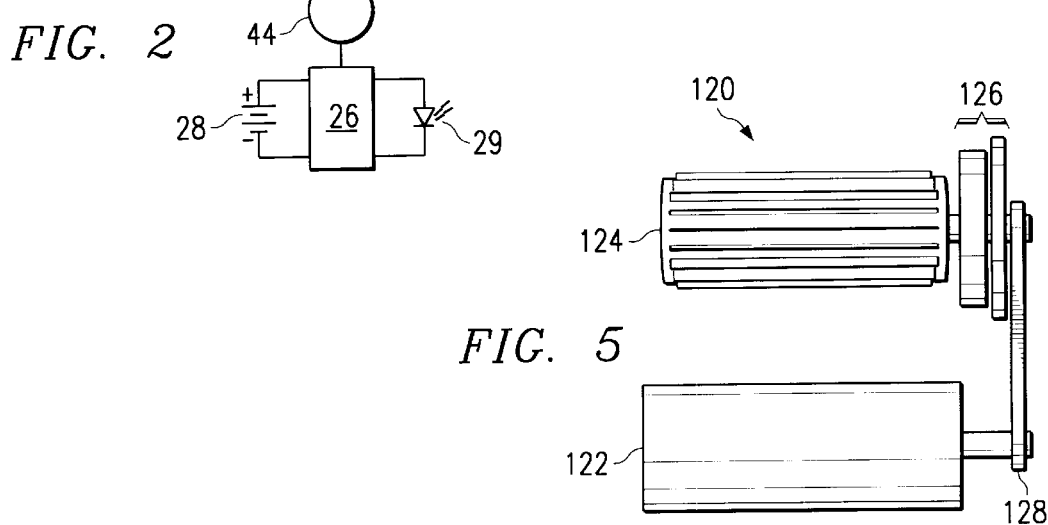
FIG. 5 is an embodiment of the recirculation pump (with impeller) of the present invention used for injecting solution into the cleaning chamber.

In accordance with the present invention, a recirculation pump is used for (1) injecting solution into a cleaning chamber and (2) causing the solution (after it swirls around to clean the contact lenses) to flow through a collecting channel and filter to remove microorganisms from the solution. FIG. 5 is a preferred embodiment of a recirculation pump in accordance with this aspect of the present invention.

Recirculation pump 120 includes motor 122 used to drive impeller 124. The rotational force provided by motor 122 is coupled to impeller 124 through belt 128. Gears 126 are used to either step up or step down the speed of rotation (as desired) in order to provide enough swirling action force in the cleaning chamber to effectively clean the contact lenses in a few minute period.

Accordingly, a system and method for cleaning and disinfecting contact lens has been provided. The system integrates effective cleaning and disinfecting functions into a single unit. The system can effectively clean and disinfect all types of contact lenses, i.e., hard, soft, etc., in a single, short cleaning cycle, and with only a small volume of solution. The invention results in a design that is not only easy and convenient for a user to operate, but one that is easy and inexpensive to manufacture as well.

Although the invention has been described above with reference to certain embodiments, it will be appreciated to one skilled in the art that the present invention can be practiced by other than the described embodiments, which are presented here for purposes of illustration and not of limitation, and that the present invention is limited only by the claims it follows.

What is claimed is:

1. A method for cleaning and disinfecting a contact lens comprising the steps of:
    (a) placing the lens in a cleaning chamber of a unit;
    (b) filling the chamber with solution;
    (c) activating an impeller for injecting solution into the cleaning chamber for cleaning said contact lens;
    (d) trapping microorganisms on a bacteriological filter; and
    (e) recirculating the solution through the unit.

2. The method of claim 1 wherein the impeller injects solution into the cleaning chamber with sufficient force to dislodge particles, films, and other deposits from the lens into the solution.

3. The method of claim 1 wherein the solution is recirculated through three chambers: (i) the cleaning chamber; (ii) a recovery chamber for receiving solution from said cleaning chamber; and (iii) a pump chamber for containing said impeller.

4. The method of claim 3 wherein step (b) further includes filling the recovery chamber and the pump chamber with said solution.

5. The method of claim 1 further including the step of replacing said filter periodically to remove the microorganisms from the unit.

6. A contact lens cleaning and disinfecting system, comprising:
    an enclosed housing including a pair of cleaning chambers, each of said chambers being concavely shaped and sized to hold one of a pair of contact lenses in a volume of ophthalmic solution;
    injection channels within said housing and operatively coupled to each of said cleaning chambers for injecting solution into the respective cleaning chamber;
    collecting channels within said housing and operatively coupled to each of said cleaning chambers for removing solution from the respective cleaning chamber;
    a bacteriological filter within said housing and operatively coupled to the collecting channels; and
    a pump within said housing and operatively coupled between the filter and the injection channels for (1) injecting solution into each cleaning chamber at a speed sufficient to remove impurities from the contact lens and (2) causing solution to flow through the collecting channels and the filter to remove microorganisms from the solution,
    whereby the pump recirculates the solution in the system through the cleaning chambers while trapping microorganisms on the filter.

7. The system of claim 6, wherein said collecting channels are located at least in part above the elevation to the solution level in said cleaning chambers to prevent backflow of the cleaning solution into said cleaning chambers.

8. The system of claim 6, wherein said pump comprises an impeller.

9. The system of claim 6, wherein the ophthalmic solution is a preservative-free saline solution.

10. The system of claim 9, wherein said system operates at ambient temperature.

11. The system of claim 6, wherein said system operates at ambient temperature.

12. The system of claim 6, wherein said housing is portable.

13. The system of claim 6, wherein said housing includes a recovery chamber operatively interposed between said collecting channels and said filter for collecting impurities removed from the contact lenses, whereby said recovery chamber allows heavy contaminants to settle on its bottom under the influence of gravity so as to remove the contaminants from the flow of solution.

14. The system of claim 6, wherein said collecting channels are located at least in part an elevation above said recovery chamber to isolate the cleaning chambers from the recovery chamber.

15. The system of claim 6, wherein said housing comprises:
    a base portion and a lid portion, said cleaning chambers, said injection channels, said collecting channels and said pump being located in said base portion; and
    a gasket carried by said lid portion, said gasket forming a seal with said base portion, when said lid portion is closed, which surrounds said cleaning chambers, injection channels, collecting channels, and pump in sealed relation.

16. The system of claim 6, wherein said injection channels comprise nozzles that are narrow with respect to the width of the cleaning chamber and that are located off-center to the cleaning chamber and coupled between the pump and the cleaning chambers, whereby turbulent swirling action of the ophthalmic solution within the cleaning chambers is provided for cleaning of the lenses.

17. The system of claim 6, wherein the bacteriological filter is a disposable bacteriological filter.

18. The system of claim 6, further comprising an electronic control for operating the pump for a predetermined period of time.

* * * * *